US00PP23864P3

(12) United States Plant Patent
Zaiger et al.

(10) Patent No.: US PP23,864 P3
(45) Date of Patent: Sep. 3, 2013

(54) INTERSPECIFIC TREE NAMED 'SUMMER COT'

(50) Latin Name: **Interspecific *Prunus* species**
Varietal Denomination: Summer Cot

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 15 days.

(21) Appl. No.: 13/374,944

(22) Filed: Jan. 25, 2012

(65) Prior Publication Data

US 2013/0191946 P1 Jul. 25, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Kent L Bell

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Regular and productive bearer of large size fruit.
2. Fruit with good flavor and eating quality.
3. Fruit maturing in the late maturity season.
4. Fruit with good storage and shipping quality.
5. Vigorous, semi-spreading tree growth.

1 Drawing Sheet

Botanical description: Interspecific *Prunus* species.
Variety denomination: 'Summer Cot'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of apricots, proprietary apricots and interspecific trees, which are known to us, and mentioned herein, 'Patterson' Apricot (U.S. Plant Pat. No. 2,877), 'Modesto' Apricot (U.S. Plant Pat. No. 2,453), 'Tracy' Apricot (U.S. Plant Pat. No. 3,062), 'Autumn Sprite' Interspecific (U.S. Plant Pat. No. 16,599), the proprietary apricots '381LH520', '73EB90', '60GA213' and the proprietary interspecifics '192LD95' and '4G436'. All of the proprietary seedling selections listed are non-patented.

STATEMENT REGARDING FEDERALLY SPONSORED RESEARCH AND DEVELOPMENT

Not applicable.

ORIGIN OF THE VARIETY

A new and distinct variety of interspecific tree, [*Prunus armeniaca*×(*Prunus armeniaca*×*Prunus salicina*)×*Prunus armeniaca*] was developed by us in our experimental orchard located near Modesto, Calif. as a first generation cross between our proprietary selections with the field identification numbers '192LD95' and '381LH520'. The seed parent '192LD95' (non-patented) originated from crosses of 'Patterson' Apricot (U.S. Plant Pat. No. 2,877), 'Modesto' Apricot (U.S. Plant Pat. No. 2,543), 'Tracy' Apricot (U.S. Plant Pat. No. 3,062) and the proprietary plumcot '4G436' (non-patented). The pollen parent '381LH520' (non-patented) originated from a second generation seedling from the cross of our proprietary selections with the field identification numbers '73EB90' (non-patented) and '60GA213' (non-patented). A large number of these crosses were grown on their own root and under close and careful observation, one such seedling exhibited desirable fruit and tree characteristics and was selected in 2002 for additional asexual propagations.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new interspecific tree [(Apricot×Plumcot)×Apricot] is of large size, with vigorous, semi-spreading growth and a regular and productive bearer of large, freestone fruit with good flavor and eating quality. The fruit is further characterized by having firm flesh, good storage and shipping quality and ripening in the late maturity season. In comparison to its seed parent '192LD95' (non-patented) the fruit of the new variety has a regular and consistent fruit production, the fruit has better flavor and is approximately 38 days later in maturity. In comparison to its pollen parent (381LH520) apricot (non-patented) the fruit of the new variety is approximately 39 days later in maturity. In comparison to the interspecific commercial variety 'Autumn Sprite' (U.S. Plant Pat. No. 16,599) the fruit of the new variety is larger in size and is approximately 10 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 9 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 9 year old specimens grown near. Modesto, Calif., with color in accordance with Munsell Book of Color.

Tree:

*Size*.—Large, usually pruned to 3 to 3.5 meters in height and width for economical harvesting of fruit, varies with different cultural practices.

*Vigor*.—Vigorous, tree growth of 1.5 to 2 meters in height the first growing season. Varies with type and fertility of soil, climatic conditions and cultural practices.

*Form*.—Semi-spreading, usually pruned to vase shape.

*Branching habit*.—Semi-spreading, crotch angle approximately 30°, increases with heavy crop load.

*Productivity*.—Productive, thinning and spacing of fruit necessary for desired marketable size. Fruit set varies with climatic conditions during blooming period.

*Bearer*.—Regular, adequate fruit set 7 consecutive years. No alternate bearing observed.

*Fertility*.—Self-fertile, sets fruit under bag.

*Density*.—Medium dense, pruned to vase shape to allow sunlight to center of tree to enhance fruit color and health of fruit spurs.

*Hardiness*.—Hardy in all stone fruit growing areas of California. Tree grown in USDA Hardiness Zone 9. Winter chilling requirement approximately 850 hours at or below 45° F.

Trunk:

*Size*.—Large. Average circumference 55.9 cm at 30.5 cm above ground on a 9 year old tree.

*Stocky*.—Medium stocky.

*Texture*.—Medium shaggy, becomes rougher with age.

*Color*.—Varies from 2.5Y 4/2 to 5Y 4/2.

Branches:

*Size*.—Medium. Average circumference 16.9 cm at 1.2 meters above ground. Crotch angle approximately 30°, increases with heavy crop load.

*Surface texture*.—New growth relatively smooth. Mature growth medium rough, becomes rougher with age.

*Lenticels*.—Average number 21 in a 25.8 sq cm area of branch. Average length 3.9 mm. Average width 2.1 mm. Color varies from 10YR 8/8 to 10YR 7/8.

*Color*.—New growth varies from 5GY 7/8 to 5GY 6/8. Mature growth varies from 7.5YR 3/2 to 7.5YR 2/2, varies with age of growth.

Leaves:

*Size*.—Medium. Average length 73.5 mm. Average width 60.0 mm.

*Form*.—Ovate.

*Apex*.—Cuspidate.

*Base*.—Obtuse.

*Margin*.—Serrate.

*Thickness*.—Medium.

*Surface texture*.—Upper surface relatively smooth, slightly indented over midrib and leaf veins, glabrous. Lower surface relatively smooth, small ridges created by midrib and pinnate venation, glabrous.

*Petiole*.—Average length 26.9 mm. Average width 1.2 mm. Longitudinally grooved, very shallow. Surface glabrous. Color varies from 5GY 7/6 to 5GY 6/6.

*Glands*.—Type — globose. Size — small. Average length 0.1 mm. Average diameter 0.1 mm. Number varies from 2 to 5, average number 3. Located primarily on the upper portion of the petiole and base of leaf blade. Color varies from 2.5GY 5/4 to 2.5GY 5/6.

*Stipules*.—None observed.

*Color*.—Upper surface varies from 5GY 5/6 to 5GY 3/6. Lower surface varies from 5GY 4/4 to 5GY 3/4. Midvein color varies from 5GY 7/4 to 5GY 7/6.

Flower buds:

*Size*.—Medium. Average length 11.6 mm. Average diameter 7.9 mm.

*Hardiness*.—Hardy in all stone fruit growing areas of California.

*Form*.—Plump, conical, becoming slightly elongated before opening.

*Pedicel*.—Average length 3.2 mm. Average width 1.3 mm. Color varies from 2.5GY 7/6 to 2.5GY 6/8.

*Color*.—Varies from 7.5RP 6/10 to 7.5RP 9/2.

*Number of buds per spur*.—Average number 4, varies from 2 to 6.

Flowers:

*Blooming period*.—Date of First Bloom Mar. 11, 2011. Date of Petal Fall Mar. 21, 2011, varies slightly with climatic conditions.

*Size*.—Medium to large. Average height 17.7 mm. Average diameter 33.7 mm.

*Petals*.—Normally 5, alternately arranged to sepals. Average length 16.3 mm. Average width 15.8 mm. Shape — orbicular, apex rounded. Base — truncate, petal narrows at point of attachment. Margin — sinuate. Both upper and lower surface glabrous. Shape — orbicular. Color varies from N 9.5/(white) to 5RP 9/2, fades with age of flower.

*Sepals*.—Normally 5, alternately arranged to petals. Shape — triangular, apex rounded to slightly pointed. Margin — entire. Average length 7.3 mm. Average width 6.4 mm. Both upper and lower surfaces glabrous. Color — upper surface varies from 7.5R 2/8 with 2.5GY 7/4. Lower surface varies from 7.5R 2/6 to 7.5R 2/8.

*Stamens*.—Average number per flower 28. Average length 13.5 mm. Filament color N 9.5/(white) to 5RP 9/12 as the flower ages.

*Pollen*.—Self-fertile, sets fruit under the bag. Color varies from 2.5Y 6/10 to 5Y 7/12.

*Pistil*.—Normally one. Surface — pubescent. Average length 20.4 mm. Position of the stigma to anthers an average of 2.4 mm above the anthers. Color varies from 10Y 8.5/4 to 10Y 8/4.

*Fragrance*.—Heavy.

*Color*.—Varies from N 9.5/(white) to 5RP 9/2, fades with age of flower.

*Number flowers per flower bud*.—Usually 1, varies from 1 to 3.

*Pedicel*.—Average length 3.9 mm. Average width 1.4 mm. Color varies from 2.5GY 6/6 to 5GY 6/6.

Fruit:

*Maturity when described*.—Firm ripe.

*Date of first picking*.—Aug. 14, 2011.

*Date of last picking*.—Aug. 21, 2011, varies slightly with climatic conditions.

*Size*.—Medium to large. Average diameter axially 57.7 mm. Average transversely in suture plane 63.0 mm. Average across suture plane 57.5 mm. Average weight 116.4 grams, varies slightly with fertility of the soil, amount of thinning and climatic conditions.

*Form*.—Slightly elongated.

*Suture*.—Slightly lipped.

*Ventral surface*.—Slightly lipped.

*Apex*.—Slightly retuse.

*Base*.—Varies from flat to slightly retuse.

*Stem cavity*.—Rounded to slightly elongated in suture plane. Average depth 5.7 mm. Average diameter 6.2 mm.

Stem:

*Size*.—Small. Average length 7.3 mm. Average diameter 4.4 mm.

*Color*.—Varies from 7.5YR 4/4 to 10YR 4/6.

Flesh:

*Ripens*.—Slightly earlier at the apex.

*Texture*.—Firm, smooth and juicy.

*Fibers*.—Few, small, tender.

*Firmness*.—Firm, comparable to commercial apricots.

*Aroma*.—Moderate.

*Amydgalin*.—Undetected.

*Eating quality*.—Very good.

*Flavor*.—Very good, a good balance between acid and sugar.

*Juice*.—Moderate amount, enhances flavor.

*Brix*.—Average Brix 13.0°, varies slightly with amount of fruit per tree and climatic conditions.

*Color*.—Varies from 7.5YR 7/12 to 7.5YR 8/10. Pit cavity varies from 7.5YR 7/10 to 7.5YR 7/12.

*Stone cavity*.—Average length 33.5 mm. Average width 28.1 mm. Average depth 10.2 mm.

Skin:

*Thickness*.—Medium.

*Surface*.—Slightly waffled.

*Pubescence*.—Moderate pubescence, short in length.

*Tendency to crack*.—None.

*Color*.—Ground color varies from 2.5Y 8/8 to 2.5Y 8/10. Lightly overspread with 5YR 6/10 to 5YR 7/10.

*Tenacity*.—Tenacious to flesh.

*Astringency*.—None.

Stone:

*Type*.—Freestone.

*Size*.—Large. Average length 29.5 mm. Average width 24.7 mm. Average depth 14.4 mm.

*Form*.—Ovoid.

*Base*.—Flat.

*Apex*.—Rounded.

*Surface*.—Slightly pitted throughout, a shallow groove on each side of suture extending from base to apex.

*Sides*.—Unequal, one side extending further from the suture plane.

*Ridges*.—Very narrow, a small ridge near groove on each side of suture.

*Tendency to split*.—None.

*Color*.—Varies from 10YR 4/6 to 10YR 5/6, when dry.

Kernel:

*Size*.—Large. Average length 20.5 mm. Average width 15.1 mm. Average depth 7.6 mm.

*Form*.—Ovoid.

*Viability*.—Viable, complete embryo development.

*Skin color*.—Varies from 10YR 6/4 TO 10YR 5/6.

Use: Dessert. Market — local and long distance.

Keeping quality: Good, held firm in cold storage 3 weeks at 38° to 42° F. without shriveling, internal breakdown of flesh or appreciable loss of eating quality.

Shipping quality: Good, minimal flesh bruising or skin scarring during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described.

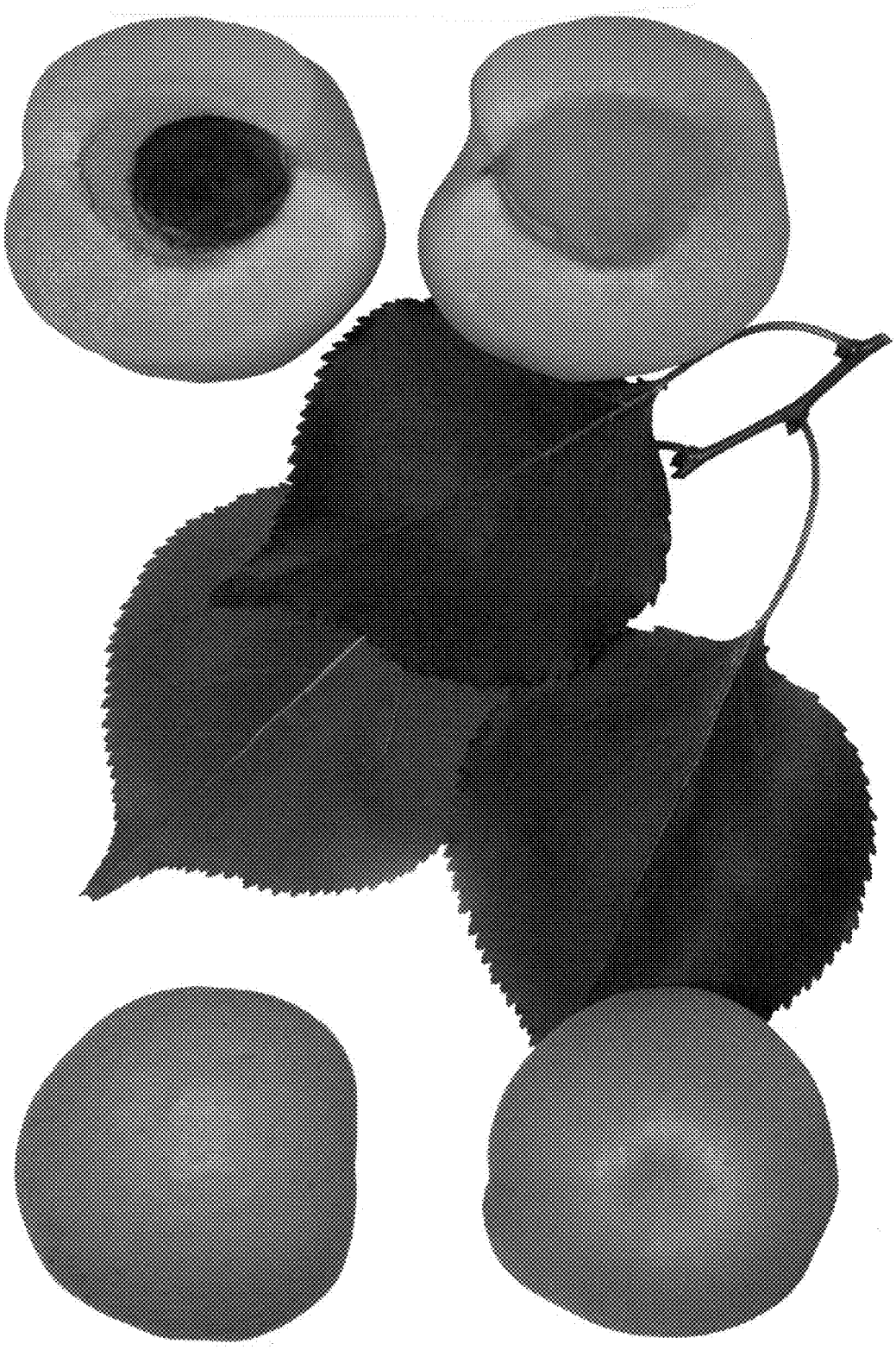

* * * * *